(12) United States Patent
Hopkins et al.

(10) Patent No.: US 11,103,255 B2
(45) Date of Patent: Aug. 31, 2021

(54) OFFSET REAMER

(71) Applicant: Zimmer, Inc., Warsaw, IN (US)

(72) Inventors: Andrew Rolfe Hopkins, Winterthur (CH); Philippe Favre, Zurich (CH)

(73) Assignee: Zimmer, Inc., Warsaw, IN (US)

( * ) Notice: Subject to any disclaimer, the term of this patent is extended or adjusted under 35 U.S.C. 154(b) by 124 days.

(21) Appl. No.: 15/552,537

(22) PCT Filed: Feb. 23, 2016

(86) PCT No.: PCT/US2016/019025
§ 371 (c)(1),
(2) Date: Aug. 22, 2017

(87) PCT Pub. No.: WO2016/137921
PCT Pub. Date: Sep. 1, 2016

(65) Prior Publication Data
US 2018/0042620 A1    Feb. 15, 2018

Related U.S. Application Data

(60) Provisional application No. 62/120,117, filed on Feb. 24, 2015.

(51) Int. Cl.
*A61B 17/16* (2006.01)
*A61B 17/17* (2006.01)

(52) U.S. Cl.
CPC ...... *A61B 17/1659* (2013.01); *A61B 17/1684* (2013.01); *A61B 17/1735* (2013.01); *A61B 17/1778* (2016.11)

(58) Field of Classification Search
CPC combination set(s) only.
See application file for complete search history.

(56) References Cited

U.S. PATENT DOCUMENTS

| | | | |
|---|---|---|---|
| 5,540,694 A | 7/1996 | Decarlo, Jr. et al. | |
| 2005/0099073 A1* | 5/2005 | Yang | H02K 7/003 310/75 R |

(Continued)

FOREIGN PATENT DOCUMENTS

WO    WO-2016137921 A1    9/2016

OTHER PUBLICATIONS

"International Application Serial No. PCT/US2016/019025, International Search Report dated Apr. 21, 2016", 4 pgs.

(Continued)

*Primary Examiner* — Matthew J Lawson
(74) *Attorney, Agent, or Firm* — Schwegman Lundberg & Woessner, P.A.

(57) ABSTRACT

A reamer operably connected to a movable drive element by a translation assembly such that the movement of the movable drive element rotates the reamer. The reamer can be sized such that the reamer can be navigated through or around soft tissue to position the reamer adjacent the defect region and angled to align the reamer with a reamer axis perpendicular to the plane of the defect region. The translation assembly can be configured to translate rotation of the movable drive element to the reamer through an opening through or around the soft tissue. The translation assembly can permit axial reaming of the defect region when the perpendicular axis is obscured by soft tissue.

8 Claims, 3 Drawing Sheets

(56) References Cited

U.S. PATENT DOCUMENTS

| | | | |
|---|---|---|---|
| 2005/0113839 A1* | 5/2005 | Yoon | A61B 17/1659 |
| | | | 606/85 |
| 2005/0273111 A1 | 12/2005 | Ferree et al. | |
| 2007/0073302 A1 | 3/2007 | Myers et al. | |
| 2012/0239043 A1* | 9/2012 | Lappin | A61B 17/1631 |
| | | | 606/80 |
| 2013/0197523 A1* | 8/2013 | Fitzpatrick | A61B 17/1684 |
| | | | 606/80 |
| 2013/0309031 A1* | 11/2013 | Winslow | A61B 17/1624 |
| | | | 408/1 R |
| 2014/0194879 A1 | 7/2014 | Koka | |
| 2015/0119891 A1* | 4/2015 | Goldberg | A61B 17/1631 |
| | | | 606/80 |
| 2016/0074047 A1* | 3/2016 | Fritzinger | A61B 17/1615 |
| | | | 606/80 |

OTHER PUBLICATIONS

"International Application Serial No. PCT/US2016/019025, Written Opinion dated Apr. 21, 2016", 6 pgs.

"International Application Serial No. PCT US2016 019025, International Preliminary Report on Patentability dated Sep. 8, 2017", 8 pgs.

\* cited by examiner

OFFSET REAMER

CLAIM OF PRIORITY

This patent application is a U.S. National Stage Filing under 35 U.S.C. 371 from International Patent Application Serial No. PCT/US2016/019025, filed Feb. 23, 2016, published on Sep. 1, 2016 as WO 2016/137921 A1, which application claims the benefit of priority, under 35 U.S.C. Section 119(e), to Andrew Hopkins et al. U.S. Patent Application Ser. No. 62/120,117, entitled "OFFSET REAMER," filed on Feb. 24, 2015, each of which is hereby incorporated by reference herein in its entirety.

TECHNICAL FIELD

This document pertains generally, but not by way of limitation, to apparatuses and related methods of use for preparing bone surfaces at the glenoid region of a scapula, or other equivalent bone structures, for receiving an implant.

BACKGROUND

The glenoid fossa of a scapula defines a cavity forming the socket of the glenohumeral "ball and socket" joint of the human shoulder. The bone surrounding the glenoid cavity can erode naturally over time, which can be accelerated by repetitive use or degenerative joint diseases. The erosion of the bone can permit undesirable shifting or movement of the head of the humerus within the socket, resulting in pain or limiting of the range of motion of the joint. The erosion of the glenoid cavity can be concentric (Type A) or asymmetric (Type B). Asymmetric erosion occurs when the bone along a side or at an edge of the socket erodes allowing the head of the humerus to slide partially or entirely out of the main socket. Excessive concentric or asymmetric erosion of the bone can cause retroversion of the joint (Type C, retroversion greater than 25 degrees). All Type C erosion and certain Type B erosion patterns, such as posterior erosion, require implantation of a glenoid implant defining an articular surface for replacing the portion of the original articular surface formed by the bone lost through erosion.

The implant surgery typically requires removal of a portion of the surrounding bone to provide a surface for mounting the implant and smooth or shape the surface for positioning the implant such that edges of the articular surface align with the edges of the articular surface defined by the bone. Replacement implants often have a spherical shape rather than being flat backed, as the spherical shape more favorably corresponds to the natural curvature of the spherical glenoid cavity. The bone at the implant site is preferably axially reamed along an axis perpendicular to the plane of the defect to provide the appropriate surface for correctly receiving and positioning the spherical shaped implant. Axial reaming also reduces the volume of bone that must be resected to correctly align the implant with the surrounding bone. Although axial reaming can efficiently prepare the bone for receiving the implant, soft tissues surrounding the glenohumeral joint prevents access to the glenoid along the axis perpendicular to the defect. Removing or shifting the soft tissue to expose the perpendicular axis proximate the glenoid can damage the soft tissue and substantially slow the healing process. The inability to align the reamer to the perpendicular axis due to the soft tissue requires the use of less effective or more invasive surgical techniques.

Overview

The present inventors have recognized, among other things, that a problem to be solved can include the inability to axially ream bone obscured by soft tissue along an axis perpendicular to the plane of the bone surface to receive the implant. In an example, the present subject matter can provide a solution to this problem, such as by providing a reamer operably connected to a drive shaft by a translation assembly such that the rotation of the drive shaft rotates the reamer. The reamer can be sized such that the reamer can be navigated through or around soft tissue to position the reamer adjacent the defect region and angled to align the reamer with a reamer axis perpendicular to the plane of the defect region. In at least one example, the reamer can be operably connected by the translation assembly to an oscillating element that pivots to oscillate the reamer about the perpendicular reamer axis. The translation assembly can be configured to translate rotation of the drive shaft to the reamer through an opening through or around the soft tissue. The translation assembly can permit axial reaming of the defect region when the perpendicular axis is obscured by soft tissue.

A reamer system for resecting an eroded portion of a glenoid region, according to an example of the present disclosure, can comprise a reamer element having a reamer shaft. The reamer shaft can be configured to be oriented along a perpendicular axis that is perpendicular to the erosion plane generally defined by the eroded portion. The reamer system can also include a drive shaft having a reamer end, the drive shaft rotatable about a rotational axis. The reamer system can also include a transfer belt arranged in a continuous loop about the reamer shaft and the reamer end of the drive shaft. The rotation of the drive shaft can be translated to the reamer shaft to rotate the reamer shaft and correspondingly the reamer element about the perpendicular reamer axis.

A reamer system for resecting an eroded portion of a glenoid region, according to an example of the present disclosure, can include a reamer element having a reamer shaft. The reamer shaft is configured to be oriented along a perpendicular reamer axis that is perpendicular to an erosion plane generally defined by the eroded portion. The reamer system can include an oscillator element that can be pivoted about a pivot axis. The reamer system can also include a transfer belt extending from the oscillator element and looped about the reamer shaft. The pivoting of the oscillator can be translated to the reamer shaft to oscillate the reamer shaft and correspondingly the reamer element about the perpendicular reamer axis.

A reamer system for resecting an eroded portion of a glenoid region, according to an example of the present disclosure, can include a reamer element having a reamer shaft and a reamer cog. The reamer shaft is configured to be oriented along a perpendicular reamer axis that is perpendicular to the erosion plane generally defined by the eroded portion. The reamer system can also include a drive shaft having a drive cog that can be engaged to the reamer cog, the drive shaft rotatable about a rotational axis. The rotation of the drive shaft can be translated to the reamer shaft by engagement of the drive cog to the reamer cog such that the reamer shaft and correspondingly the reamer element are rotated about the perpendicular reamer axis.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
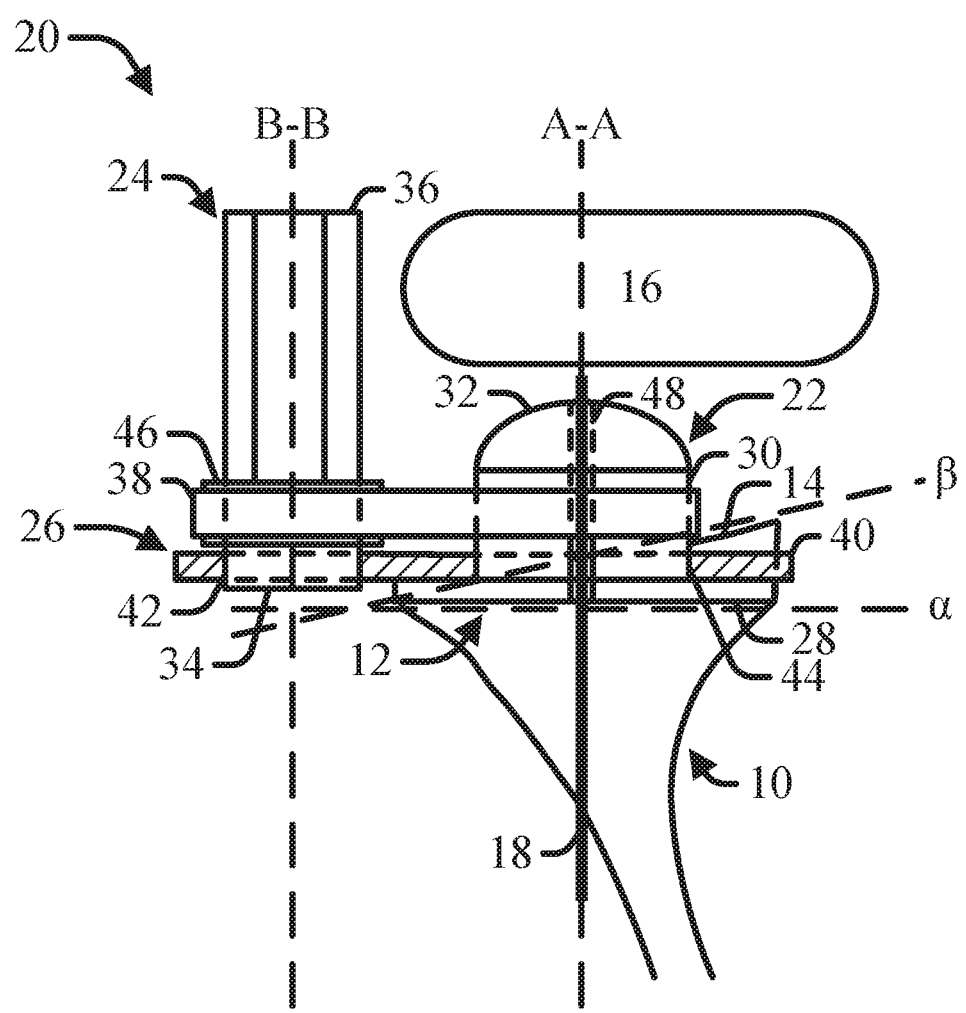
FIG. 1 is a schematic diagram of a reamer system having a transfer belt for rotating a reamer according to an example of the present disclosure.
Figure 2:
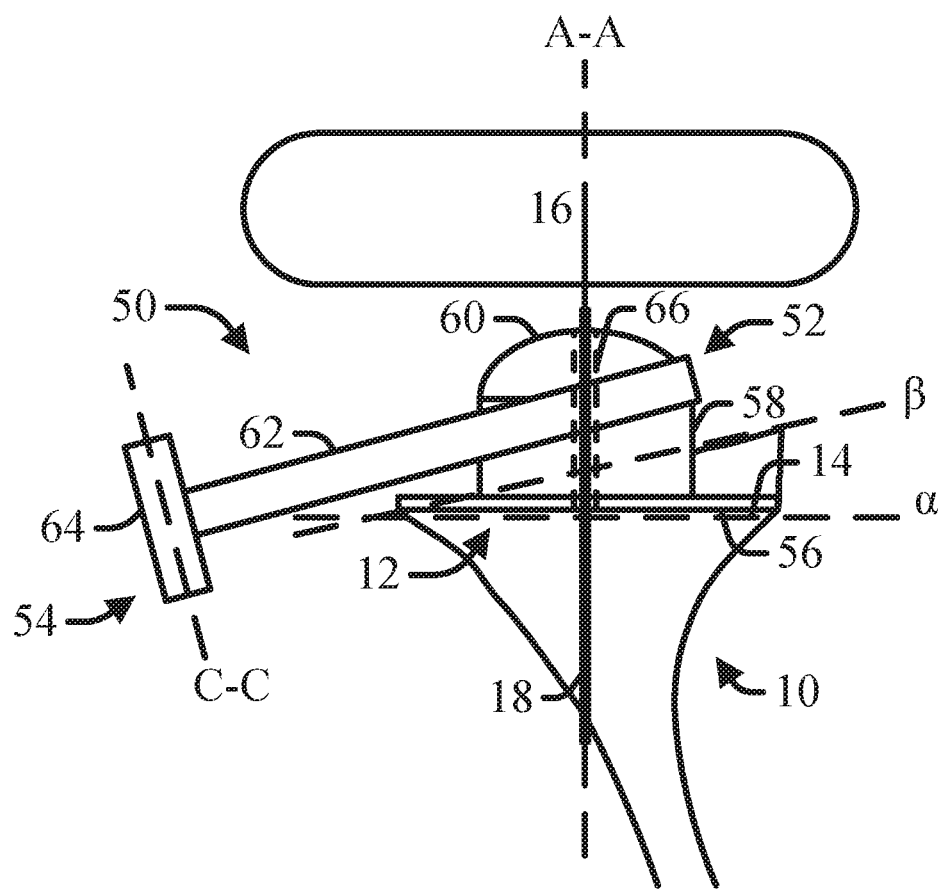
FIG. 2 is a schematic diagram of a reamer system having an oscillator system for oscillating a reamer according to an example of the present disclosure.
Figure 3:
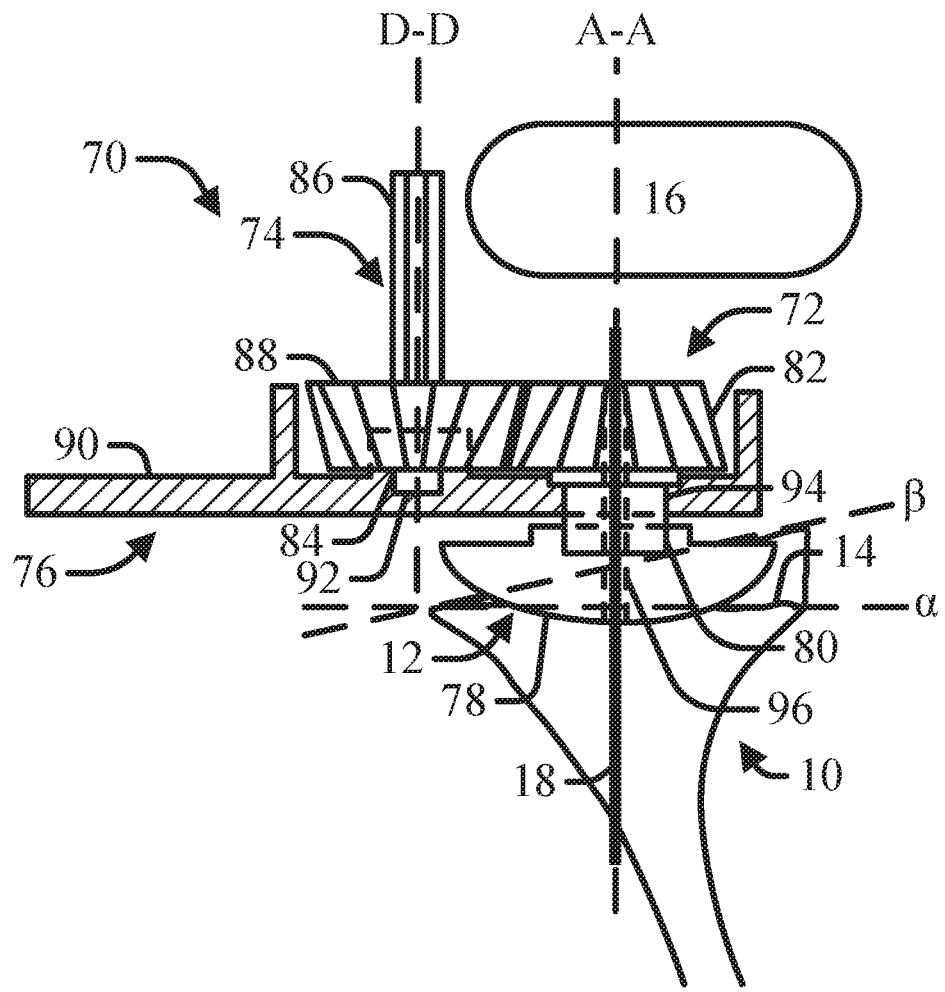
FIG. 3 is a schematic diagram of a reamer system having intermeshing cogs for rotating a reamer with a drive shaft according to an example of the present disclosure.

A schematic diagram of a glenoid region 10 of a scapula is depicted in FIGS. 1-3 for illustrating examples of the present subject matter. As depicted, the glenoid region 10 comprises an eroded surface 12 generally defining a plane α. A perpendicular reamer axis A-A extends from the plane α defined by the eroded surface 12. The glenoid region 10 also comprises an un-eroded surface 14 generally defining a plane β. Soft tissue 16 can be positioned around the glenoid region 10, and can be an obstacle to axial reaming of the eroded surface 12 along the axis A-A. The description herein and depiction in the figures of the glenoid region 10 and surrounding soft tissue 16 are not intended to be limiting, but rather are presented for illustrating examples of the present subject matter depicted in the corresponding figures.

As depicted in FIG. 1, a reamer system 20, according to an example of the present subject matter, can include a reamer 22, a drive shaft 24 and a translation assembly 26. The reamer 22 can be positioned against the eroded surface 12. The translation assembly 26 can operably connect the drive shaft 24 to the reamer 22 such that rotation of the drive shaft 24 rotates the reamer 22 about the perpendicular reamer axis A-A to axially ream the eroded surface 12. The drive shaft 24 can be configured to rotate about an axis B-B. In at least one example, the rotational axis B-B of the drive shaft 24 is parallel to the perpendicular reamer axis A-A as depicted in FIG. 1.

In an example, the reamer 22 can include a reamer element 28 and a reamer shaft 30. The reamer element 28 can define a planar reamer surface (as depicted in FIGS. 1 and 2), a hemispherical reamer surface (as depicted in FIG. 3), or other curved or shaped surfaces for reaming the eroded surface to the desired shape. The reamer shaft 30 extends from the reamer element 28 and can be operably connected to the translation assembly 26 such that rotation of the drive shaft 24 rotates the reamer shaft 30 and correspondingly the reamer element 28.

In an example, the drive shaft 24 can comprise a gear end 34 and a rotator end 36. The drive shaft 24 can define an outer radius and centered about rotational axis B-B. The rotator end 36 can be configured to be engaged by a rotator apparatus to rotate the drive shaft 24 about rotational axis B-B. The rotator apparatus can comprise a motor, a lever handle, a ratchet handle, a hand tool or other apparatus for rotating the drive shaft 24 about axis B-B. The drive shaft 24 can have a circular cross-section or a polygonal cross-section (as depicted in FIG. 1). In at least one example, the polygonal faces of the drive shaft 24 can be gripped by the rotator apparatus to rotate the drive shaft 24.

In an example, the translation assembly 26 can comprise a transfer belt 38 and a positioning plate 40. The positioning plate 40 can define a drive opening 42 and a reamer opening 44. The drive opening 42 can be sized to rotatably receive the gear end 34 of the drive shaft 24 such that the drive shaft 24 is rotatable within the drive opening 42. The reamer opening 44 can be sized to rotatably receive the reamer shaft 30 such that the reamer shaft 30 is rotatable within the reamer opening 44. The positioning plate 40 can maintain the alignment of the drive shaft 24 and the reamer shaft 30 as the drive shaft 24 and the reamer shaft 30 rotate. In at least one example, the positioning plate 40 can maintain the parallel orientation of the drive shaft 24 to the reamer shaft 30 at least during rotation of the reamer shaft 30 by the drive shaft 24 as depicted in FIG. 1. In certain examples, the reamer shaft 30 can include a rounded cap 32 positioned opposite the reamer element 28. In at least one example, the transfer belt 38 can rotatably engage the rounded head cap 32. In this configuration, the rotational axis B-B can be angled relative to the perpendicular reamer axis A-A. In an example, the head cap 32 can include a retention element positioned at the end of the head cap 32. The retention element can comprise a plate or other extending feature that prevents slippage of the transfer belt 38 from the rounded head cap 32.

As depicted in FIG. 1, in an example, the transfer belt 38 can be arranged in a continuous loop extending around the gear end 34 of the drive shaft 24 and the reamer shaft 30 such that rotation of the drive shaft 24 by the rotator apparatus rotates the reamer shaft 30. The drive shaft 24 and the reamer shaft 30 can have different outer radii to allow the reamer shaft 30 to rotate at a different rotational speed from the drive shaft 24. If the outer radius of the drive shaft 24 is greater than the outer radius of the reamer shaft 30, the reamer shaft 30 will rotate at a greater rotational speed than the drive shaft 24. If the outer radius of the drive shaft 24 is less than the outer radius of the reamer shaft 30, the reamer shaft 30 will rotate at a slower rotational speed than the drive shaft 24.

In at least one example, a gear 46 can be positioned on the drive shaft 24 proximate the gear end 34 to change the effective outer radius of the drive shaft 24. The gear 46 can define a secondary outer radius that alters the effective outer radius of the drive shaft 24. In at least one example, the gear 46 can be interchanged with another gear 46 to change the effective outer radius of the drive shaft 24.

In at least one example, the translation assembly 26 can comprise a chain instead of or in addition to the transfer belt 38. In this configuration the gear end 34 of the drive shaft 24 and the reamer shaft 30 can comprise teeth for engaging the chain to facilitate transfer of the rotational motion of the drive shaft 24 to the reamer shaft 30. Similarly, the gear 46 can include teeth for engaging the chain to transfer rotational motion of the drive shaft 24 to the translation assembly 26.

In an example, the reamer shaft 30 can define a guide shaft 48 for receiving a K-wire 18. As illustrated in FIG. 1, the K-wire 18 can be driven into the glenoid region 10 along the perpendicular reamer axis A-A and such that a portion of the K-wire 18 extends from the eroded surface 12 along the perpendicular reamer axis A-A. The protruding portion of the K-wire 18 can be inserted into the guide shaft 48 such that the reamer shaft 30 is aligned with the perpendicular reamer axis A-A. In certain examples, the reamer 22 can be operated free hand by the operator without a K-wire 18 guide or other guide element.

Referring to FIG. 1, a method for preparing an eroded surface 12 for receiving an implant can include providing or obtaining a reamer system 20 having a reamer 22, a drive shaft 24 and a translation assembly 26 operably linking the reamer 22 to the drive shaft 24. The method can further include positioning a reamer element 28 of the reamer 22 against the eroded surface 12 such that a reamer shaft 30 extends from the reamer element 28 along a perpendicular reamer axis A-A that is perpendicular to a plane generally defined by the eroded surface 12. In at least one example, the method can include inserting a K-wire 18 into the eroded surface 12 such that a portion of the K-wire 18 extends along the perpendicular reamer axis A-A. In this configuration, the extended portion of the K-wire 18 can be inserted into a guide shaft 48 of the reamer shaft 30 to align the reamer shaft 30 with the perpendicular reamer axis A-A. The method can also include rotating the drive shaft 24 about a rotational axis B-B, wherein a transfer belt 38 is looped around the drive shaft 24 and the reamer shaft 30 such that the rotation of the drive shaft 24 rotates the reamer shaft 30. In at least one example, the rotational axis B-B of the drive shaft 24 can be parallel to and offset from the perpendicular reamer axis A-A.

As depicted in FIG. 2, a reamer system 50, according to an example of the present subject matter, can include a reamer 52 and an oscillator assembly 54. The reamer 52 can be positioned against the eroded surface 12. The oscillator assembly 54 can be operably connected to the reamer 52 and configured to pivot about an oscillating axis C-C to oscillate the reamer 52 about perpendicular reamer axis A-A. In at least one example, the oscillating axis C-C can be angled relative to the perpendicular reamer axis A-A as illustrated in FIG. 2.

In an example, the reamer 52 can include a reamer element 56 and a reamer shaft 58. The reamer element 56 can define a planar reamer surface (as depicted in FIGS. 1 and 2), a hemispherical reamer surface (as depicted in FIG. 3), or other curved or shaped surfaces for reaming the eroded surface to the desired shape. The reamer shaft 58 can extend from the reamer element 56 and can be operably connected to the oscillator assembly 54 such that pivoting of the oscillator assembly 54 oscillates the reamer shaft 58 and correspondingly the reamer element 56. In certain examples, the reamer shaft 58 can include a rounded head cap 60 positioned opposite the reamer element 56.

In an example, the oscillator assembly 54 can comprise a transfer belt 62 and an oscillator element 64. The oscillator element 64 can be configured to pivot about pivot axis C-C. The transfer belt 62 can be arranged to loop around the reamer shaft 58 such that the pivoting of the oscillator element 64 oscillates the reamer shaft 58 and correspondingly the reamer element 56. The pivot axis C-C can be oriented parallel to the perpendicular reamer axis A-A. In at least one example, the transfer belt 62 can rotatably engage the rounded head cap 60 as illustrated in FIG. 2. In this configuration, the pivot axis C-C can be angled relative to the perpendicular reamer axis A-A.

In an example, the reamer shaft 58 can define a guide shaft 66 for receiving a K-wire 18. As illustrated in FIG. 1, the K-wire 18 can be driven into the glenoid region 10 along the perpendicular reamer axis A-A and such that a portion of the K-wire 18 extends from the eroded surface 12 along the perpendicular reamer axis A-A. The protruding portion of the K-wire 18 can be inserted into the guide shaft 66 such that the reamer shaft 58 is aligned with the perpendicular reamer axis A-A.

Referring to FIG. 2, a method for preparing an eroded surface 12 for receiving an implant can include providing or obtaining a reamer system 50 having a reamer 52 and an oscillator assembly 54 operably linked to the reamer 52. The method can further include positioning a reamer element 56 of the reamer 52 against the eroded surface 12 such that a reamer shaft 58 extends from the reamer element 56 along a perpendicular reamer axis A-A that is perpendicular to a plane generally defined by the eroded surface 12. In at least one example, the method can include inserting a K-wire 18 into the eroded surface 12 such that a portion of the K-wire 18 extends along the perpendicular reamer axis A-A. In this configuration, the extended portion of the K-wire 18 can be inserted into a guide shaft 66 of the reamer shaft 58 to align the reamer shaft 58 with the perpendicular reamer axis A-A. The method can also include pivoting an oscillator element 64 about a pivot axis C-C, wherein a transfer belt 62 extends from the oscillator element 64 and is looped about the reamer shaft 58 such that the pivoting of the oscillator element 64 oscillates the reamer shaft 58. In at least one example, the pivot axis C-C of the oscillator element 64 can be transverse to the perpendicular reamer axis A-A.

As depicted in FIG. 3, a reamer system 70, according to an example of the present subject matter, can include a reamer 72, a drive shaft 74 and a translation assembly 76. The reamer 72 can be positioned against the eroded surface 12. The translation assembly 76 can operably connect the drive shaft 74 to the reamer 72 such that rotation of the drive shaft 74 rotates the reamer 72 about the perpendicular reamer axis A-A to axially ream the eroded surface 12. The drive shaft 74 can be configured to rotate about an axis D-D. In at least one example, the rotational axis D-D of the drive shaft 74 can be parallel to the perpendicular reamer axis A-A as depicted in FIG. 3.

In an example, the reamer 72 can include a reamer element 78 and a reamer shaft 80. The reamer element 78 can define a planar reamer surface (as depicted in FIGS. 1 and 2), a hemispherical erosion surface (as depicted in FIG. 3), or other curved or shaped surface for eroding the eroded surface to the desired shape. The reamer shaft 80 can extend from the reamer element 78 and can include a reamer cog 82 operably connected to the translation assembly 76 such that rotation of the drive shaft 74 rotates the reamer shaft 80 and correspondingly the reamer element 78.

In an example, the drive shaft 74 can comprise a gear end 84 and a rotator end 86. The drive shaft 74 can comprise a generally cylindrical shape defining an outer radius and centered about rotational axis D-D. The rotator end 86 can be configured to be engaged by a rotator apparatus to rotate the drive shaft 74 about rotational axis D-D. The rotator apparatus can comprise a motor, a lever handle, a ratchet handle, a hand tool or other apparatus for rotating the drive shaft 74 about axis D-D. The drive shaft 74 can have a circular cross-section or a polygonal cross-section (as depicted in FIG. 3). In at least one example, the polygonal faces of the drive shaft 74 can be gripped by the rotator apparatus to rotate the drive shaft 74. The gear end 84 of the drive shaft 74 can include a drive cog 88 oriented to interface with the reamer cog 82.

In an example, the translation assembly 76 can comprise a positioning plate 90. The positioning plate 90 can define a drive opening 92 and a reamer opening 94. The drive opening 92 can be sized to rotatably receive the gear end 84 of the drive shaft 74 such that the drive shaft 74 is rotatable within the drive opening 92. The reamer opening 94 can be sized to rotatably receive the reamer shaft 80 such that the reamer shaft 80 is rotatable within the reamer opening 94. The positioning plate 90 can maintain the engagement of the drive cog 88 of the drive shaft 74 to the reamer cog 82 of the reamer shaft 80 such that rotation of the drive shaft 74 rotates the reamer shaft 80 as illustrated in FIG. 3.

In an example, the reamer shaft 80 can define a guide shaft 96 for receiving a K-wire 18. As illustrated in FIG. 1, the K-wire 18 can be driven into the glenoid region 10 along the perpendicular reamer axis A-A and such that a portion of the K-wire 18 extends from the eroded surface 12 along the perpendicular reamer axis A-A. The protruding portion of the K-wire 18 can be inserted into the guide shaft 48 such that the reamer shaft 80 is aligned with the perpendicular reamer axis A-A.

Referring to FIG. 3, a method for preparing an eroded surface 12 for receiving an implant that can include providing or obtaining a reamer system 70 having a reamer 72 including a reamer cog 82 positioned on a reamer shaft 80. The reamer system 70 can also include a drive shaft 74 having a drive cog 88 operably linked to the reamer cog 82. The method can further include positioning a reamer element 78 of the reamer 72 against the eroded surface 12 such that the reamer shaft 80 extends from the reamer element 78 along a perpendicular reamer axis A-A that is perpendicular to a plane generally defined by the eroded surface 12. In at least one example, the method can include inserting a K-wire 18 into the eroded surface 12 such that a portion of the K-wire 18 extends along the perpendicular reamer axis A-A. In this configuration, the extended portion of the K-wire 18 can be inserted into a guide shaft 96 of the reamer shaft 80 to align the reamer shaft 80 with the perpendicular reamer axis A-A. The method can also include rotating the drive shaft 74 about a rotational axis D-D, wherein the intermeshed drive cog 88 and reamer cog 82 translates rotation of the drive shaft 74 to the reamer shaft 80. In at least one example, the rotational axis D-D of the drive shaft 74 can be offset and parallel to the perpendicular reamer axis A-A.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A reamer system for resecting an eroded portion of a glenoid region, the eroded portion generally defining an erosion plane, comprising:
   a reamer element having a rounded head cap and a reamer shaft defining a first outer radius, wherein the reamer shaft is configured to be oriented along a perpendicular reamer axis that is perpendicular to the erosion plane, and wherein the reamer shaft defines a guide shaft for receiving a K-wire configured to extend from the glenoid region along the perpendicular reamer axis;

a movable drive element comprising a drive shaft rotatable about a rotational axis, the drive shaft defining a second outer radius; and a translation assembly for translating motion of the drive element to the reamer shaft to move the reamer shaft and correspondingly the reamer element about the perpendicular reamer axis;

wherein the first and second outer radii are different to allow the reamer shaft to rotate at a different rotational speed than the drive shaft; and wherein the translation assembly comprises a transfer belt that loops around the drive shaft of the movable drive element and the rounded head cap of the reamer element to translate motion from the drive shaft to the reamer shaft and correspondingly the reamer element.

2. The reamer system of claim 1, wherein the rotational axis is angled relative to the perpendicular reamer axis.

3. The reamer system of claim 1, wherein the reamer element has at least one of a planar surface and a curved surface configured to contact the eroded portion of the glenoid region.

4. The reamer system of claim 1, wherein the reamer element has a planar surface configured to contact the eroded portion of the glenoid region, and wherein the rounded head cap comprises a curved outer surface facing opposite the planar reamer surface.

5. The reamer system of claim 3, wherein the rounded head cap comprises a curved outer surface facing opposite the at least one of the planar surface and the curved surface configured to contact the eroded portion of the glenoid region.

6. The reamer system of claim 1, further comprising a positioning plate, the positioning plate comprising:
   a reamer opening for rotatably receiving the reamer shaft; and
   a drive opening for rotatably receiving the movable drive element.

7. The reamer system of claim 1, wherein the reamer element has a hemispherical surface.

8. The reamer system of claim 1, wherein the transfer belt is arranged in a continuous loop.

* * * * *